United States Patent [19]
Sasaki et al.

[11] Patent Number: 5,457,492
[45] Date of Patent: Oct. 10, 1995

[54] LIGHT SOURCE DEVICE FOR AN IMAGE PROCESSOR

[75] Inventors: Yasuhiro Sasaki; Yasuaki Morita; Toru Yanagisawa; Tetsuo Hotta; Shinsaku Tsuchida; Keizo Shinano, all of Tokorozawa, Japan

[73] Assignee: Citizen Watch Co., Ltd., Tokyo, Japan

[21] Appl. No.: 275,539

[22] Filed: Jul. 15, 1994

[30] Foreign Application Priority Data

Jul. 15, 1993 [JP] Japan ................................ 5-197927
Jun. 28, 1994 [JP] Japan ................................ 6-146051

[51] Int. Cl.⁶ .................................................. H04N 5/232
[52] U.S. Cl. ........................ 348/126; 348/131; 348/370; 356/237
[58] Field of Search ............................... 348/131, 132, 348/87, 92, 126, 370; 356/237; H04N 5/232

[56] References Cited

U.S. PATENT DOCUMENTS

| | | | |
|---|---|---|---|
| 5,148,375 | 9/1992 | Horikami | 348/126 X |
| 5,197,105 | 3/1993 | Uemura et al. | 348/126 X |
| 5,369,492 | 11/1994 | Sugawara | 348/126 X |

*Primary Examiner*—Wendy R. Greening
*Attorney, Agent, or Firm*—Dennison, Meserole, Pollack & Scheiner

[57] ABSTRACT

A light source device for an image processor has a plurality of LEDs which are disposed below a television camera. A shelter plate is disposed above the light source so as to prevent light emitted from the light source from directly entering the television camera. A cylindrical light transmitting barrel is provided, extending from the television camera to a position sufficiently close to an object to be detected.

11 Claims, 7 Drawing Sheets

LIGHT SOURCE DEVICE FOR AN IMAGE PROCESSOR

BACKGROUND OF THE INVENTION

The present invention relates to a light source device for an image processor which converts a picture image detected by an industrial television (ITV) into a binary numeral for further processing, and more particularly to a light source device of an image processor adapted to detect a solder leveler formed on a print circuit board.

The image processor which converts a picture image signal picked up by the ITV into a two-value data comprising a high level signal and a low level signal (1 and 0) is now used in various technical fields. In an automatic mounting system of electronic devices, the image processor is used for detecting the mounting positions of the devices and positions of standard marks on a print circuit board.

Referring to FIG. 1, showing an example of a conventional image processor, an ITV camera 2 is mounted on a robot 1 at an appropriate vertical position dependent on a focal length of the camera. A light source device 11 is mounted on the ITV camera 2 around a lens barrel 4 thereof. The light source device 11 has a light source such as a cold-cathode tube and/or LEDs which emits light, and a diffusing plate for transmitting and diffusing the light. In order that diffused light transmitted through the diffusing plate may have a sufficient quantity of light, a light source capable of emitting a relatively large quantity of light is selected.

The diffused light from the light source device 11 is projected onto a standard mark 10 formed on a print circuit board 3. However, only the light within a range indicated by dot-dash lines 11a between the light source device 11 and the standard mark. 10 in FIG. 1 is applied to the standard mark 10. The direction of light beam to be projected on the mark 10 is the direction included in the range between the lines 11a.

Since the standard mark 10 is made of a conductive material such as a piece of copper foil, the surface thereof is flat. Therefore, in the case where the position of the mark 10 is detected, a comparatively sufficient quantity of light is reflected on the flat surface, although the light in the only small range defined by the lines 11a is projected on the mark. Consequently, an appropriate picture image can be obtained by the ITV camera. Hence no serious trouble occurs.

The image processor is also used for detecting the position of a conductive member coated with solder, that is, a solder leveler. The thickness of the solder coated on the conductive member is often irregular and hence the surface of the solder leveler is uneven. Namely, as shown in FIG. 4, the surface of a solder leveler 12 formed on the standard mark 10 is uneven in most cases. Moreover, due to the surface tension of the molten solder, the surface of the leveler is smooth. Therefore, diffused reflection on the surface occurs very little. Consequently, the directions of the reflected light is determined by the incident angle of each light beam. Hence, depending on the inclination of the surface of the solder leveler, or the existence of pinholes, the light reflected on the surface, for example, at a point B shown in FIG. 4 is hardly detected by the ITV camera 2. As a result, the detected image data for the solder leveler 12 recognized by the image processor fails to show the portion corresponding to the point B.

More particularly, as described above, the light applied to the solder leveler 12 from the conventional light source device 11 is in the range between the lines 11a in FIG. 1. Showing light as being applied to a point A in FIG. 4, the light within a hatched area defined by lines 11b is projected on the point A. An incident light Ai reflected on the point A becomes a reflected light Ao which is directed toward the ITV camera 2. If the inclination of the solder surface becomes larger than that of the point A, the light Ai does not reflect to the ITV camera. In order to reflect to the ITV camera on such a large inclination surface, the light Ai must be applied at a larger incident angle. In other words, a more inclined direction than the illustrated angle of the light Ai can be picked up by the camera. However, since the light having a maximum incident angle is the incident light Ai in the conventional light source device 11, none of the beams reflected on such a steep surface are fed to the ITV camera 2, so that the image processor forms an incomplete image data having gaps.

As described above, if the inclination of the surface of the solder leveler is large or pinholes are formed on the surface, the quantity of light fed to the ITV camera decreases. Hence the images are darkened, thereby further causing the gaps to be formed when converted into a two-value data.

When the image processor recognizes such an incomplete image, the detected contour or the center of the image inevitably differs from the actual contour or the correct center of the object, thereby causing error in the measurements. In order to solve such a problem, there has been proposed an image processor provided with a system where the gaps in the image are compensated through an exclusive operation so as to obtain a full image. However, not only is such an image processor expensive, but in many cases, it is difficult to detect the gap included in the image. Hence the conventional image processor system is insufficient to eliminate the defect.

SUMMARY OF THE INVENTION

An object of the present invention is to provide a light source device where light projected on an object such as a solder leveler is reflected to an ITV camera without regard to inclinations of the surface of the object or existence of pinholes, thereby enabling to accurately detect the object.

Another object is to provide a light source device wherein the components of the emitted light substantially parallel to the surface of the object may be increased, thereby to prevent the picture image from darkening.

According to the present invention, there is provided a light source device for an image processor having a television camera comprising a light source disposed below the television camera, a shelter member disposed above the light source so as to prevent light emitted from the light source from directly entering the television camera, a cylindrical light transmitting barrel extending from the television camera to a position adjacent an object to be detected, and a diffusing plate having an opening at a central portion thereof and secured to an inside wall of the light transmitting barrel at a portion below the light source for diffusing the light emitted from the light source.

The inside wall of the light transmitting barrel has an opaque pear-skin surface for causing diffused reflection of the light emitted from the light source.

An auxiliary light source such as an electroluminescent element may be provided at a lower portion in the light transmitting barrel.

A light transmitting member such as an optical fiber may be provided in the light transmitting barrel for transmitting the light of the light source to a lower end portion of the light transmitting barrel.

In accordance with the light source device of the present invention, the light transmitting barrel from which light is emitted is sufficiently extended to face the object, thereby widely diffusing the light from the entire caliber of the light transmitting barrel. Hence most of the reflected light enters the ITV camera despite the large inclination of the surface of the object or the existence of the pinholes. Moreover, the quantity of light falling on the object is increased, thereby enabling one to use a light source emitting a relatively small quantity of light.

In addition, when a surface light source or an additional light source is added, the components of light which are substantially parallel to the surface of the object can be increased. Hence the quantity of light reflected on the object is increased, thereby preventing the picture image from becoming dark even if the inclination of the surface is large, or when there is a pinhole, thus enabling the image processor to recognize a complete image.

These and other objects and features of the present invention will become more apparent from the following detailed description with reference to the accompanying drawings.

DETAILED DESCRIPTION OF THE PREFERRED EMBODIMENT

Figure 1:
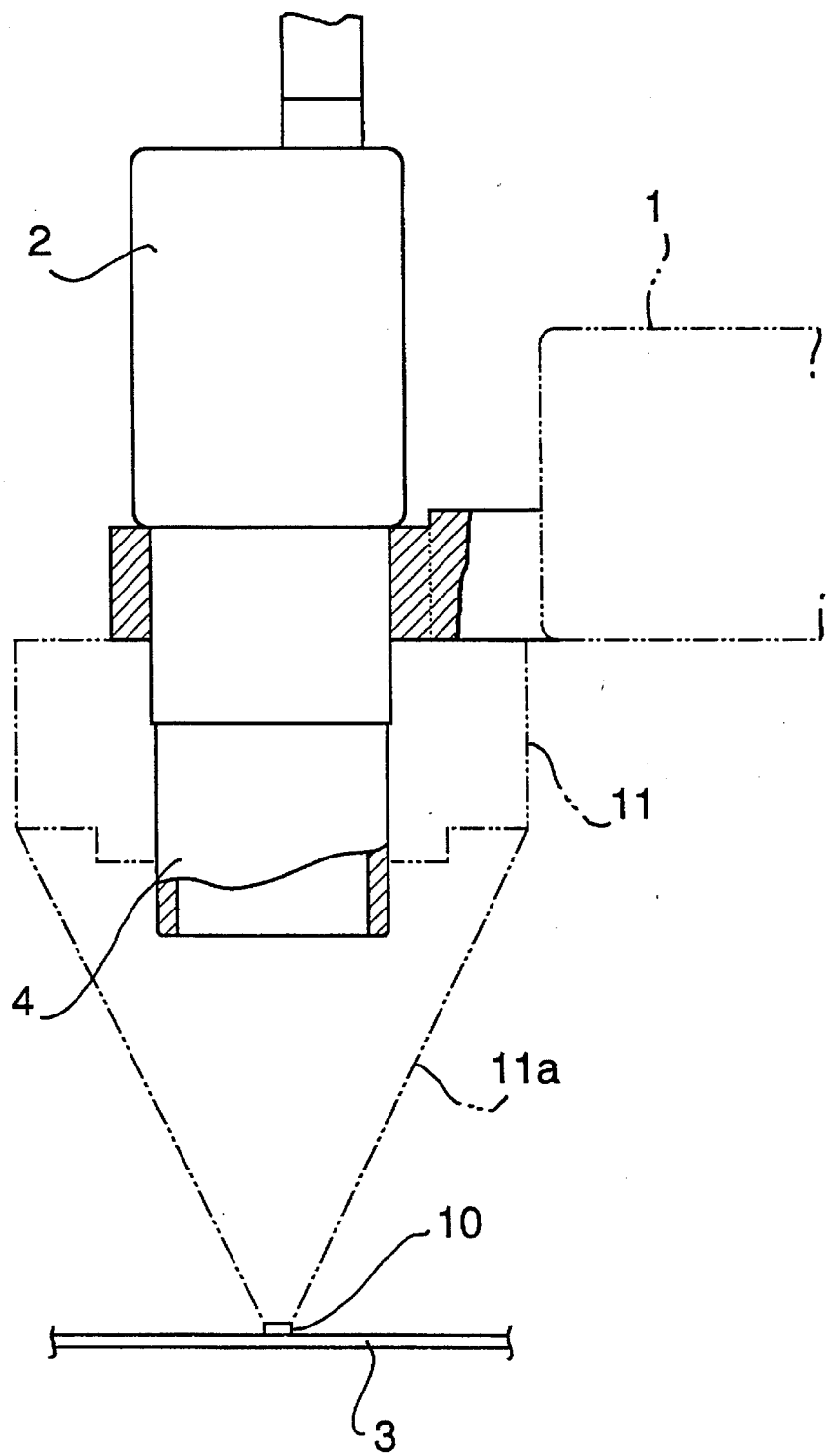
FIG. 1 is a sectional view of a conventional light source device for an image processor.
Figure 2:
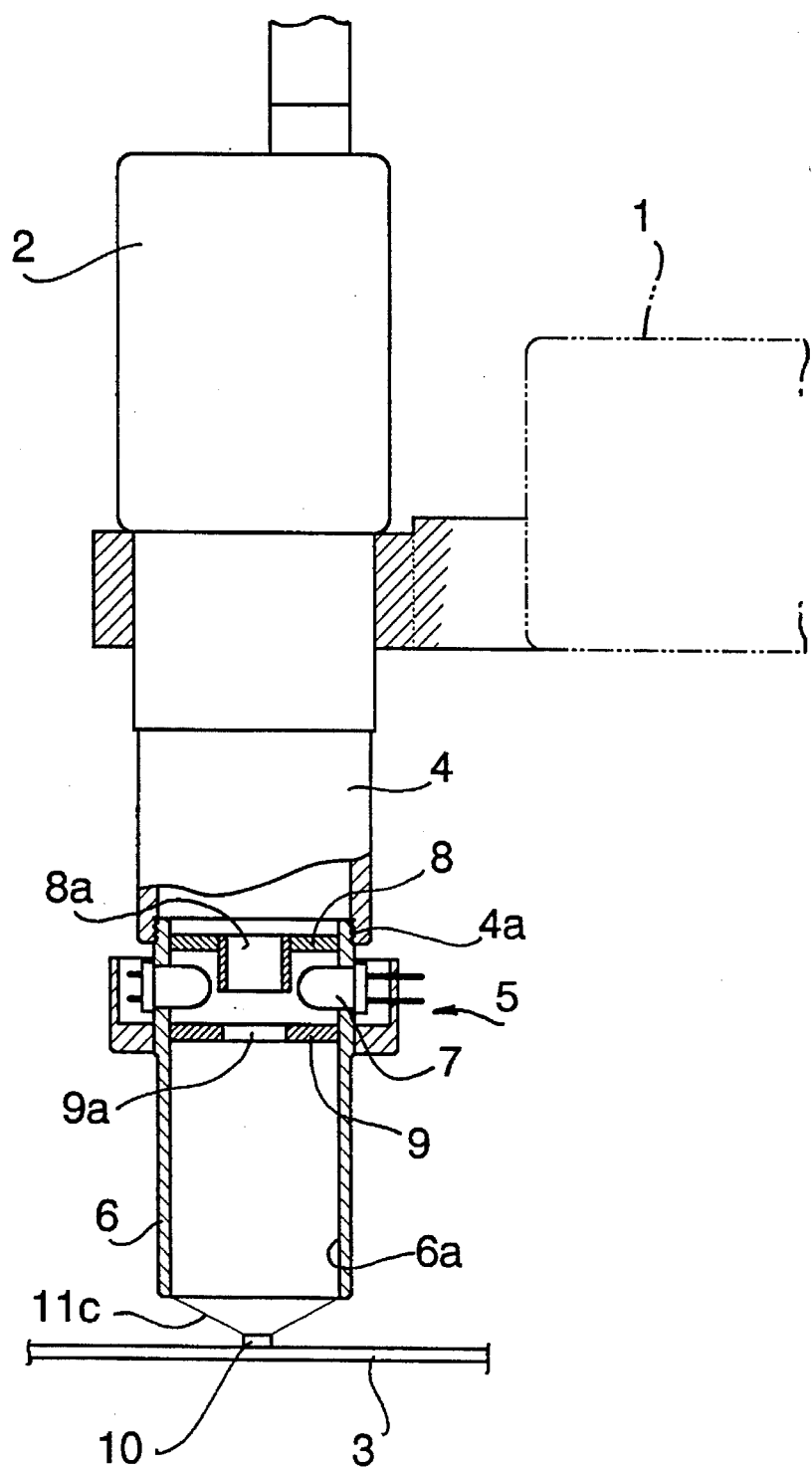
FIG. 2 is a fragmentary sectional view of a light source device for the image processor according to the present invention.

FIG. 2 shows a light source device according to the present invention. The same references as those in FIG. 1 designate the same parts in FIG. 2.

The robot 1 is adapted to move the ITV camera 2 of the image processor in the X and Y directions of the print circuit board 3. A screw thread 4a is formed on an inside wall of a lower portion of the lens barrel 4, and a light source device 5 of the present invention is attached to the lens barrel 4 by means of the screw thread 4a.

The light source device 5 comprises a light transmitting opaque barrel 6 screwed in the screw thread 4a of the lens barrel 4, a plurality of LEDs 7 as a light source annually arranged in the light transmitting barrel 6 at a portion adjacent the upper edge of the light transmitting barrel 6. A shelter plate 8 having a light transmitting opening 8a is secured to the inside wall of the light transmitting barrel 6 at a portion above the LEDs 7. A diffusing plate 9 having a light transmitting opening 9a is provided under the LEDs 7. An inner wall 6a of the light transmitting barrel 6 has a pear-skin (rough surface) reflector surface for causing diffused reflection.

Figure 3:
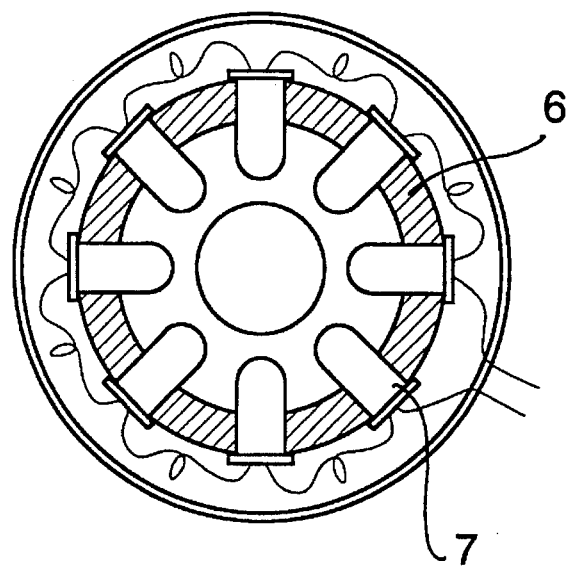
FIG. 3 is a sectional view showing light sources provided in the light source device of FIG. 2.

The radially disposed LEDs 7 are connected with one another as shown in FIG. 3 and are controlled by a controller (not shown) so as to be lighted. The shelter plate 8 prevents the light of the LEDs from directly entering the ITV camera 2, thereby preventing causing noises in the image processor. As long as the upper portions of LEDs are covered, the shelter plate 8 may be formed into various shapes other than the planar shape shown in the figure. For example, the shelter plate 8 may be a reflector plate enclosing an upper side of each LED except for a lower portion thereof.

The light transmitting openings 8a and 9a are formed in the center portions of the shelter plate 8 and the diffusing plate 9, respectively, so that light reflected on the standard mark 10 formed on the print circuit board 3 may reach the ITV camera 2. A transparent glass or a lens may be provided in the light transmitting openings.

The lower end of the light transmitting barrel 6 is located at a position which is very close to the standard mark as an object. For example, the distance between the end of the barrel 6 and the standard mark 10 is 2 mm to 5 mm.

In operation, the light emitted from the LEDs 7 is diffused by the diffusing plate 9. The diffused light is further reflected at random on the inner surface of the light transmitting barrel 6 which is formed into the pear-skin reflector surface. The diffused light is thus directly projected on the standard mark 10 on the print circuit board 3. Hence the light applied on the standard mark 10 is diffused light projected from the entire caliber of the opening of the light transmitting barrel 6 which is considerably closely situated to the object to be detected.

Figure 4:
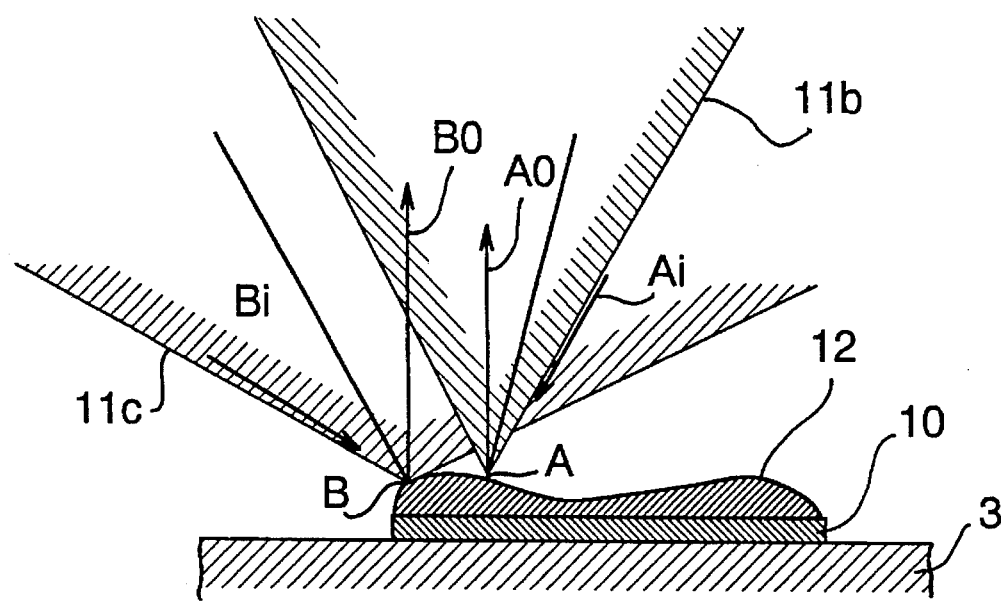
FIG. 4 is an illustration describing relations between emitted light beams and the reflections thereof.

Since the lower end of the light transmitting barrel 6 is close to the object, the range between the incident angles becomes wide as shown by a reference 11c in FIG. 4. The range corresponds to a hatched area which is shown as the range of light applied to the point B in FIG. 4. As the illustration shows, even at the point B of the solder leveler 12 where the inclination is large, a reflected light Bo falls in a range directed toward the ITV camera 2 including the incident light Bi. As a result, the solder leveler 12 is depicted as a complete image by a binary numeral, so that the position of the standard mark 10 is accurately detected.

Even in the light device 5 as the first embodiment of the present invention, there may remain a small undetected portion along the periphery of the solder leveler 12 of FIG. 4. Namely, the light reflected on the periphery is not directed to the ITV camera 2. Such a portion is very small and only formed evenly along the periphery of the solder leveler, so that the undetected portion can generally be neglected as a position detecting error. If it is undesirable to neglect the error, the upper surface of the solder leveler is ground with abrasive such as sand paper to form a coarse surface, thereby causing a diffused reflection of the light. Thus, areas of the surface, the reflection therefrom is not directed to the ITV camera 2, are diminished.

In a conventional system, polishing of the surface has already been carried out to form a smoother surface, hence decreasing the portion which does not reflect light aimed toward the ITV camera 2. However, in the present invention, there is no need to further smooth the surface so that only a rough grinding is sufficient.

The light emitted from the light source, is lead through the light transmitting barrel 6, the lower opening of which is positioned adjacent the object, so that the quantity of light diffused outside decreases. Therefore, a light source emitting a relatively small quantity of light suffices. Thus, instead of the expensive cold-cathode tube, which emits a large quantity of light, inexpensive LEDs can be used.

In order to increase the incident angle of the light falling on the object, it is preferable to increase the caliber of the lower opening of the light transmitting barrel 6 as much as possible. On the other hand, in order to decrease the quantity of light diffusing outside, the opening is made as small as possible. It is hence necessary to determine the caliber of the barrel 6 in consideration of these inconsistent problems.

In the light source device 5 of the first embodiment, the quantity of components of light substantially parallel to the surface of the object is smaller than the components of light substantially perpendicular to the surface. In other words, when the inclination of the surface of the solder leveler is large, or pinholes are formed in the solder leveler, the picture image becomes dark, so that gaps may be formed in the two-value data for the detected image. The second to fifth embodiments shown in FIGS. 5 to 8, respectively, are intended to increase the components which are substantially parallel to the surface of the object. In each of the figures, the same references as those in FIG. 2 designate the same parts so that the descriptions thereof are omitted.

Figure 5:
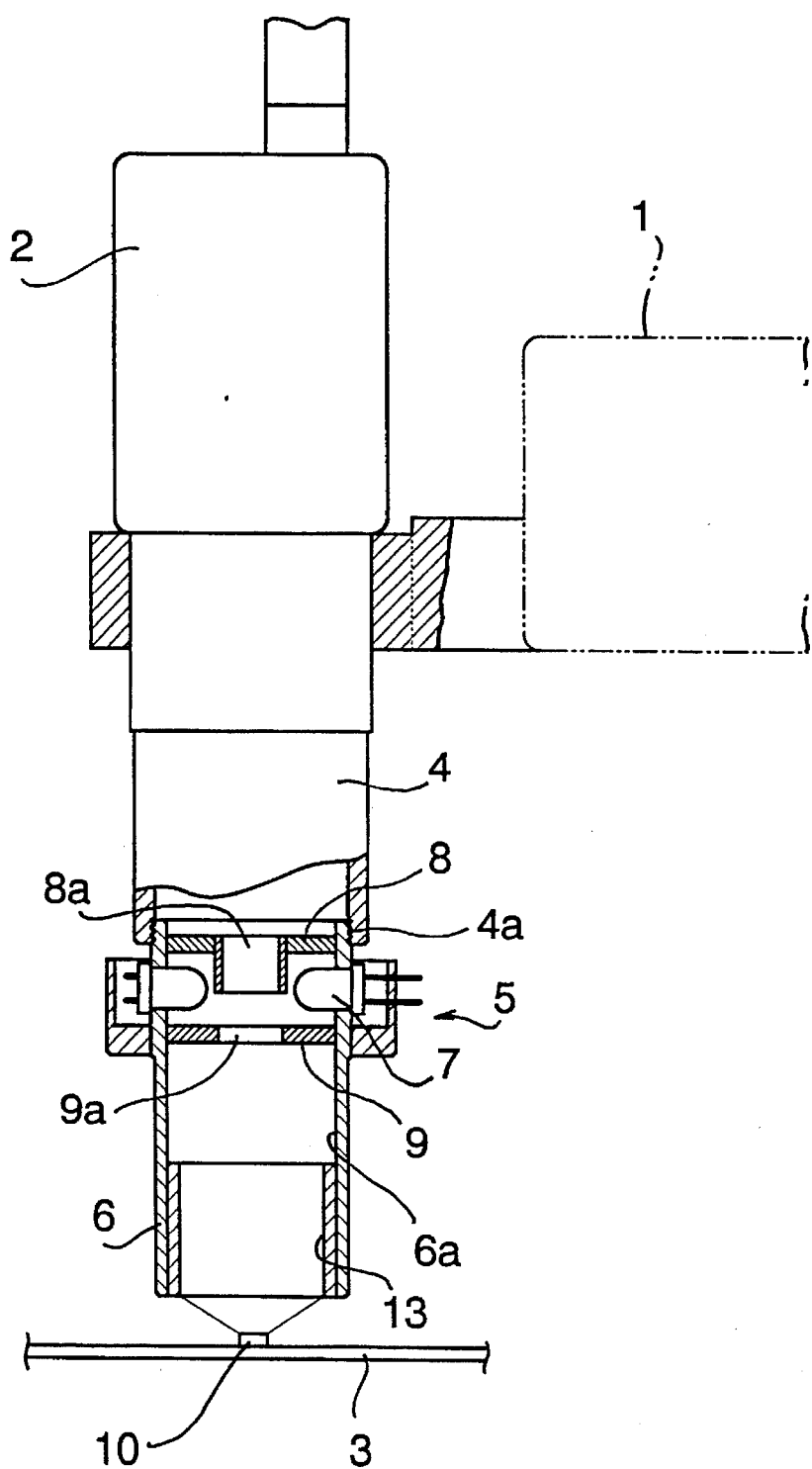
FIGS. 5 to 8 are sectional views of various embodiments of the light source device according to the present invention.

Referring FIG. 5, the light source device 5 of the second embodiment of the present invention is provided with a cylindrical surface light source 13 in addition to the light source of LEDs 7. The surface light source 13 comprises an electroluminescent element, fixed to the inner wall 6a of the light transmitting barrel 6 at a lower portion thereof. The inner wall of the surface light source 13 has a pear-skin surface to cause the diffused reflection of light. The surface light source 13 is applied with electric current and has a capacity for emitting a predetermined quantity of light.

The surface light source 13 emits light from the entire surface thereof. The emitted light is substantially parallel to the surface of the standard mark 10. Thus the horizontal components of light are increased so that sufficient quantity of light is transmitted to the ITV camera even if the surface of the solder leveler 12 is largely inclined, or pinholes are formed. Hence, no gaps are formed in the binary numerals for the detected image.

Figure 6:
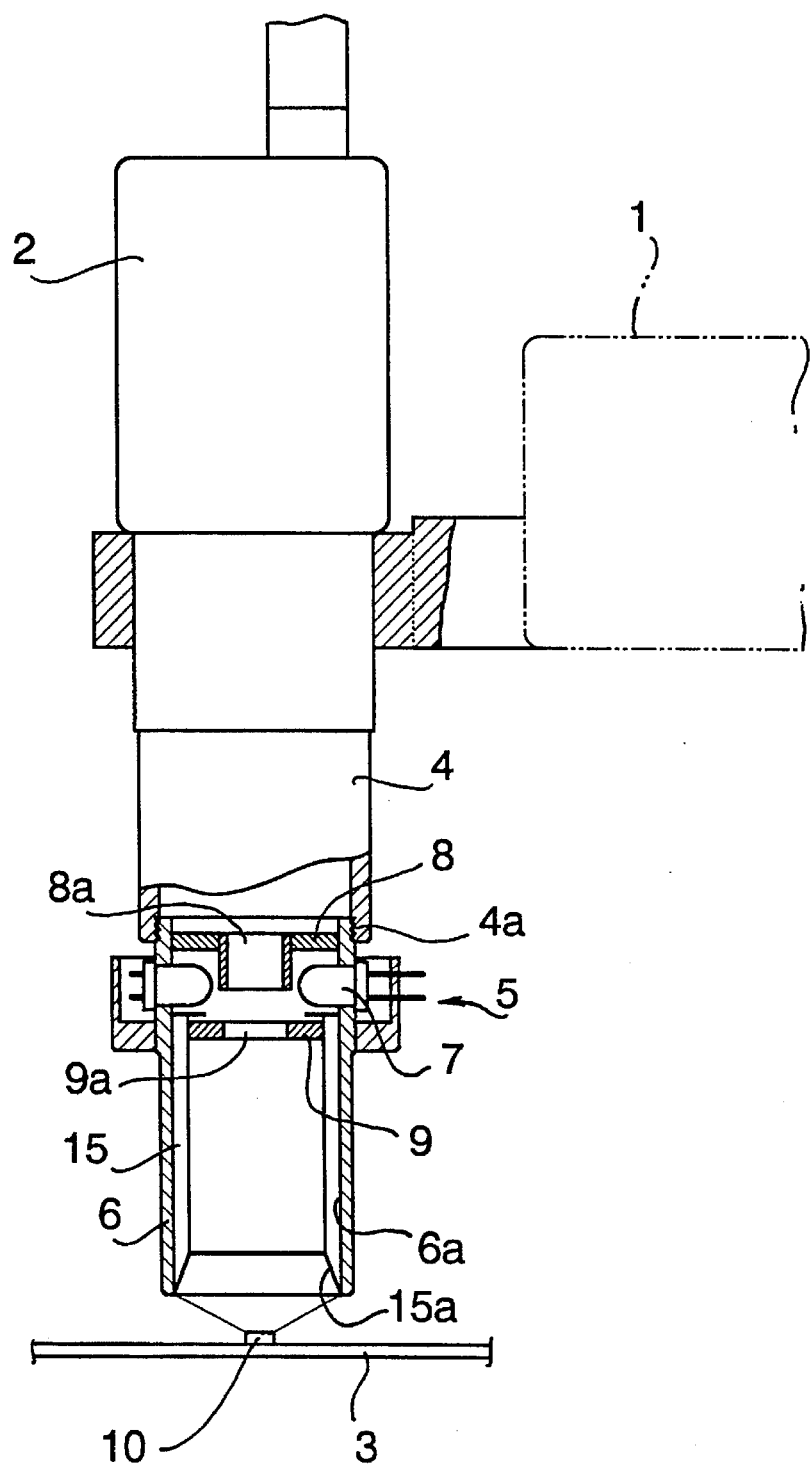

In the third embodiment shown in FIG. 6, a light transmitting member 15 comprising a cylindrical acrylic resin plate is attached to the inner surface of a lower portion of the light transmitting barrel 6. The inner surface of the light transmitting member 15 has a pear-skin surface so as to cause diffused reflection. The light transmitting member 15 has a light emitting portion 15a which flares out downwardly. The light emitted from the LEDs 7 passes through the light transmitting member 15 and is radiated from the light emitting portion 15a toward the standard mark 10.

Figure 7:
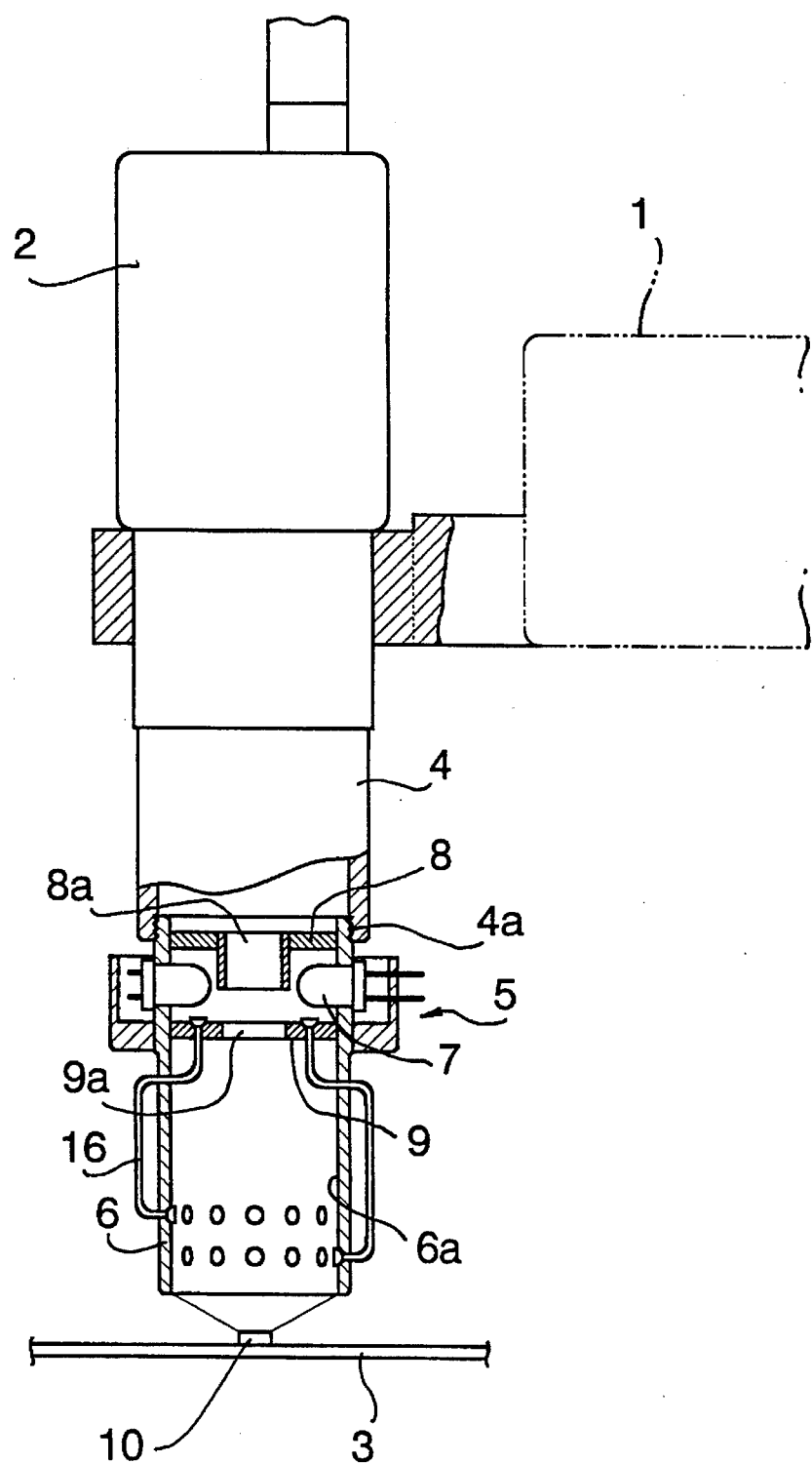

Referring to FIG. 7, showing the fourth embodiment of the present invention, a plurality of optical fibers 16 are annually disposed between the LEDs 7 and a lower end of the light transmitting barrel 6. The upper end of each optical fiber 16 is disposed adjacent the LEDs 7. An intermediate portion of the optical fiber is extended outside the barrel 6. The lower end re-enters the barrel 6 so as to face the lower end to the inner space of the barrel, thereby emitting a light in the horizontal direction. The inner wall 6a of the light transmitting barrel 6 has a pear-skin surface. Thus, the third and fourth embodiments provide the same effect as that of the second embodiment shown in FIG. 5.

Figure 8:
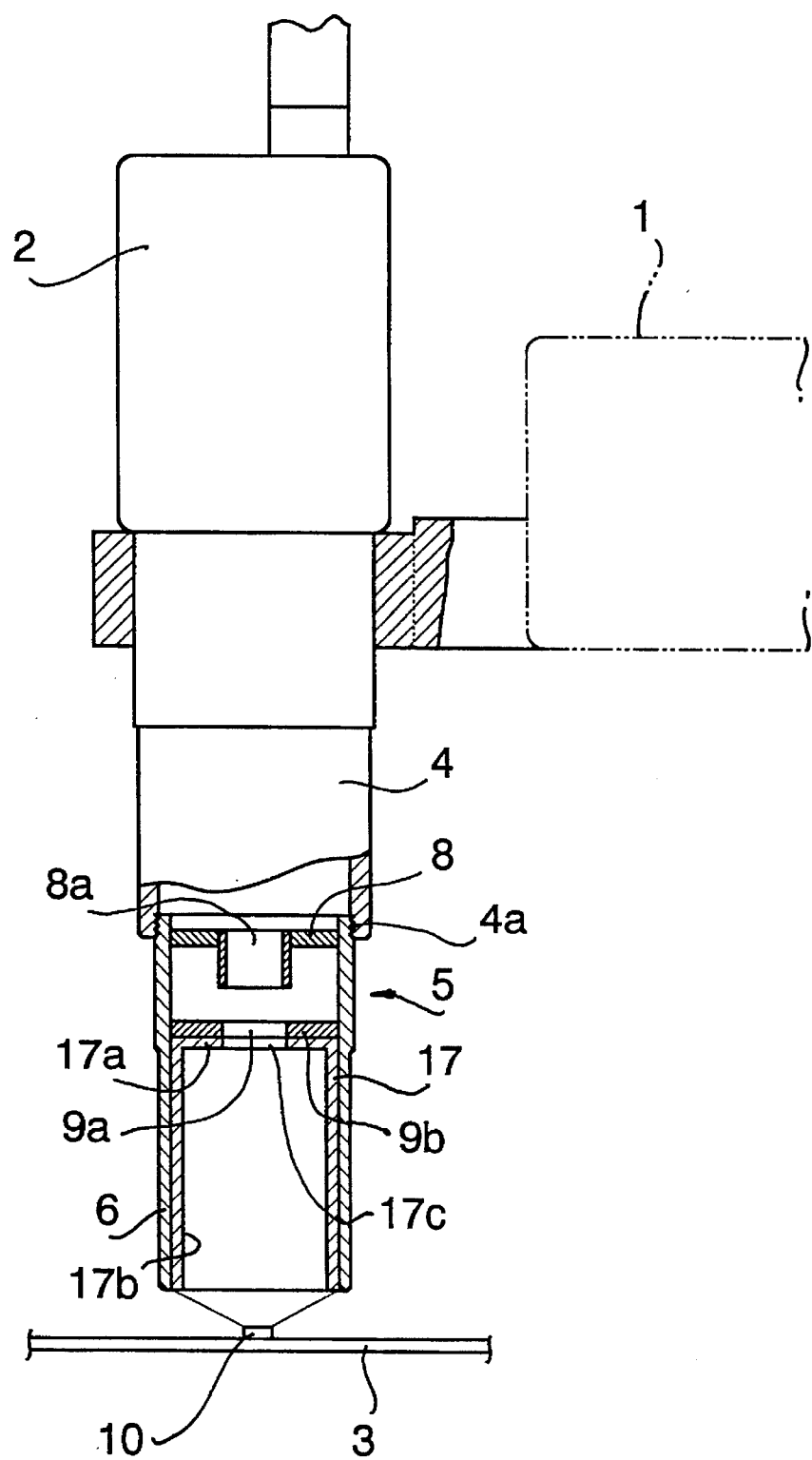

Referring to FIG. 8, the fifth embodiment of the present invention has a cylindrical surface light source member 17 comprising an electroluminescent element which covers the entire inner surface of the light transmitting barrel 6. The surface light source member 17 has an annular plate 17a having a central opening 17c at the upper inner portion thereof. A cylindrical body 17b of the light source member 17 is fixed to the barrel 6 and the annular plate 17a is fixed to a mounting plate 9b attached to the inner wall of the light transmitting barrel 6. LEDs are not provided in this embodiment.

Since an electroluminescent element having a large capacity is used as the light source 17, the same effect as those of the previous embodiments is obtained although the LEDs are omitted in the present embodiment.

Although the present invention has been described in accordance with the image processor converting the picture image into two-value data, the invention may be arranged to produce an image data represented by multiple values.

From the foregoing, it will be understood that the present invention provides a light source device for an image processor wherein the light projected to the object to be detected is diffused from lower opening of the light transmitting barrel which is sufficiently close to the object. Accordingly, the light reflected on the object is substantially completely transmitted to the ITV camera despite the large inclinations and pinholes formed on the surface of the object.

The light emitted from the light source is lead through the light transmitting barrel without diffusing outside of the barrel, so that it is possible to use an inexpensive light source capable of emitting a small quantity of light. Moreover, the components of light which are substantially parallel to the surface of the object are increased, so that gaps in the detected image data are diminished.

While the invention has been described in conjunction with preferred specific embodiment thereof, it will be understood that this description is intended to illustrate and not limit the scope of the invention, which is defined by the following claims.

What is claimed is

1. A light source device for an image processor having a television camera, comprising:

a cylindrical light transmitting barrel comprising opaque material and vertically extending from the television camera to a position adjacent an object to be detected;

a light source disposed in the cylindrical light transmitting barrel at an upper portion thereof;

shelter member means disposed above the light source for preventing light emitted from the light source from directly entering the television camera; and annular diffusing plate means having an opening at a central portion thereof, said annular diffusing plate means being disposed in the cylindrical light transmitting barrel and secured to an inside wall of the cylindrical light transmitting barrel at a portion below the light source for diffusing the light emitted from the light source.

2. The light source device according to claim 1, wherein an inside wall of the cylindrical light transmitting barrel has a pear-skin surface for causing diffused reflection of the light emitted from the light source.

3. The light source device according to claim 1, wherein a lower end of the light transmitting barrel is disposed at a position of 2 mm to 5 mm from the object.

4. The light source device according to claim 1, further comprising:

an auxiliary light source provided at a lower portion in the cylindrical light transmitting barrel.

5. The light source device according to claim 1, further comprising light transmitting member means provided in the cylindrical light transmitting barrel for transmitting the light of the light source to a lower end portion of the cylindrical light transmitting barrel.

6. The light source device according to claim 4, wherein the auxiliary light source comprises a surface light source.

7. The light source device according to claim 5, wherein the light transmitting member means comprises a cylindrical acrylic resin plate.

8. The light source device according to claim 5, wherein the light transmitting member means comprises a plurality of optical fibers.

9. The light source device according to claim 6, wherein the surface light source comprises an electroluminescent element.

10. A light source device for an image processor having a television camera, comprising:

a cylindrical light transmitting barrel comprising opaque material and extending from the television camera to a position adjacent an object to be detected;

a surface light source provided in the cylindrical light transmitting barrel at an upper portion thereof;

annular diffusing phase means having an opening at a central portion thereof and secured to an inside wall of said cylindrical light transmitting barrel at a portion below said surface light source for diffusing the light emitted from said surface light source; and shelter member means disposed above the surface light source for preventing light emitted from the light source from directly entering the television camera.

11. The light source device according to claim 10, wherein the surface light source is an electroluminescent element.

* * * * *